(12) United States Patent
Prelogar et al.

(10) Patent No.: US 10,575,082 B2
(45) Date of Patent: Feb. 25, 2020

(54) UNIVERSAL ADJUSTABLE EAR TIP

(71) Applicant: Piearcings, LLC, Kansas City, MO (US)

(72) Inventors: Barrett Prelogar, Lake Ozark, MO (US); Patsy Nigh, Lake Ozark, MO (US)

(73) Assignee: Piearcings, LLC, Kansas City, MO (US)

( * ) Notice: Subject to any disclaimer, the term of this patent is extended or adjusted under 35 U.S.C. 154(b) by 0 days.

(21) Appl. No.: 16/162,073

(22) Filed: Oct. 16, 2018

(65) Prior Publication Data

US 2019/0116412 A1 Apr. 18, 2019

Related U.S. Application Data

(60) Provisional application No. 62/572,642, filed on Oct. 16, 2017.

(51) Int. Cl.
| | | |
|---|---|---|
| *H04R 25/00* | (2006.01) | |
| *H04R 1/10* | (2006.01) | |
| *A61F 11/10* | (2006.01) | |
| *A61F 11/08* | (2006.01) | |
| *A61F 11/12* | (2006.01) | |

(52) U.S. Cl.
CPC ......... *H04R 1/1016* (2013.01); *H04R 1/1025* (2013.01); *H04R 1/1041* (2013.01); *H04R 1/1058* (2013.01); *A61F 11/08* (2013.01); *A61F 11/10* (2013.01); *A61F 11/12* (2013.01); *H04R 25/652* (2013.01); *H04R 25/656* (2013.01); *H04R 25/659* (2019.05); *H04R 2420/07* (2013.01)

(58) Field of Classification Search
CPC .. H04R 1/1041; H04R 1/1016; H04R 1/1025; H04R 25/652; H04R 25/60; H04R 25/65; A61F 11/08; A61F 11/10
USPC .................................. 381/74, 370, 379–380
See application file for complete search history.

(56) References Cited

U.S. PATENT DOCUMENTS

| | | | | |
|---|---|---|---|---|
| 6,094,494 A | * | 7/2000 | Haroldson | ........... H04R 25/456 381/322 |
| 7,362,875 B2 | * | 4/2008 | Saxton | ................. H04R 25/652 381/322 |
| 7,477,756 B2 | * | 1/2009 | Wickstrom | .......... H04R 1/1016 381/328 |

(Continued)

FOREIGN PATENT DOCUMENTS

KR 101473474 B1 1/2015

*Primary Examiner* — Disler Paul
(74) *Attorney, Agent, or Firm* — Erickson Kernell IP, LLC

(57) ABSTRACT

An audio device for insertion into an ear canal of a user that includes an adjustable ear tip. The ear tip is formed by a sleeve disposed on a body of the audio device with a first end of the sleeve coupled to an output end of the body. An opposite second end of the sleeve is coupled to a collar that encircles and threadably engages the body. In a retracted state, the sleeve lies alongside an exterior surface of the body. Rotation of the collar relative to the body moves the collar axially along the body and flexes the sleeve radially outward away from the body. An extent of rotation of the collar is selectable to provide a radial dimension of the sleeve and thus the ear tip that provides a suitable fit of the audio device with a user's ear canal.

17 Claims, 5 Drawing Sheets

(56) References Cited

U.S. PATENT DOCUMENTS

| | | | | |
|---|---|---|---|---|
| 7,639,831 | B2* | 12/2009 | Hagberg | H04R 1/1016 381/328 |
| 8,340,338 | B2* | 12/2012 | Mlodzikowski | H04R 1/1016 381/328 |
| 9,210,498 | B1* | 12/2015 | Shaffer | H04R 1/1016 |
| 2010/0166241 | A1* | 7/2010 | Sabio | H04R 25/656 381/328 |
| 2012/0155689 | A1* | 6/2012 | Milodzikowski | H04R 1/1016 381/379 |

* cited by examiner

UNIVERSAL ADJUSTABLE EAR TIP

CROSS-REFERENCE TO RELATED APPLICATIONS

This application claims the benefit of U.S. Provisional Patent Application No. 62/572,642, filed Oct. 16, 2017, the disclosure of which is hereby incorporated herein in its entirety by reference.

BACKGROUND

Wireless technologies and miniaturization of computer hardware have exploded in recent years to enable a variety of new applications. One such application is the wearable audio device or headphone. Traditional wearable audio devices employed a pair of speakers tethered by respective wires to a single headphone jack, which could be plugged into an audio player or other device. Subsequent audio devices eliminated the wires tethering the speakers to the audio player moving instead to a wireless communication system. Early wireless audio devices employed a wired connection between speaker units, but more recent technologies enable completely wireless and physically separate speaker units, which can be installed in or on the ear.

Both wired and wireless audio devices that are configured to be supported by or in the ear of the user have been provided in numerous forms that promote characteristics such as retention of the audio device in the ear, comfort to the user, increased audio quality, and blocking or canceling of environmental noise. However, available audio devices are unable to adequately adapt to the range of sizes of users' ears and/or ear canals without provision of multiple adaptors in varying sizes that can be selectively coupled to the audio device by the user based on the user's desired fit. For example, audio devices might be provided with a set of ear tips in small, medium, and large sizes. The user must then select and apply a desired one of the ear tips to the audio device to achieve a desired fit. These ear tips are generally small in overall size and can be easily lost and/or damaged, and they may still fail to provide the fit desired by the user.

SUMMARY

Exemplary embodiments are defined by the claims below, not this summary. A high-level overview of various aspects thereof is provided here to introduce a selection of concepts that are further described in the Detailed-Description section below. This summary is not intended to identify key features or essential features of the claimed subject matter, nor is it intended to be used in isolation to determine the scope of the claimed subject matter. In brief, this disclosure describes an in-ear audio device with an integral, adjustable ear tip.

The audio device, referred to interchangeably herein as an earbud, is configured for use by insertion at least partially into the ear canal of a user and includes an output end through which an audio output is directed and a base end opposite the output end. The earbud may include a bullet-like shape with the output end being positioned at the apex of the bullet shape. The earbud includes an ear tip sleeve comprised of a pliable, resilient material that is disposed to cover at least a portion of the exterior surface of the earbud between the output end and the base.

In a minimum size configuration or retracted state, the ear tip sleeve lies alongside and/or against the surface of the earbud with a leading edge thereof retained on the earbud at or near the output end. A trailing edge of the ear tip sleeve is moveable axially along the exterior surface of the earbud toward the leading edge. Movement of the trailing edge toward the leading edge causes the portion of the ear tip sleeve between the two edges to flex and expand or mushroom radially outwardly from the earbud; the greater the movement of the trailing edge toward the leading edge the greater the extent to which the ear tip sleeve flexes outward and the larger the overall diameter of the ear tip sleeve.

Movement of the trailing edge relative to the leading edge of the ear tip sleeve can be provided by a tracked coupling between the ear tip sleeve and the body of the earbud such that rotation of the ear tip sleeve relative to the earbud causes axial movement of the trailing edge. In another embodiment, the trailing edge may be moved by sliding parallel to the axis of the earbud. One or more detents or stops may be provided to indicate and/or maintain positions of the trailing edge along the length of the earbud.

DESCRIPTION OF THE DRAWINGS

Illustrative embodiments are described in detail below with reference to the attached drawing figures, and wherein.

DETAILED DESCRIPTION

The subject matter of select exemplary embodiments is described with specificity herein to meet statutory requirements. But the description itself is not intended to necessarily limit the scope of claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described. The terms "about," "approximately," and "substantially" as used herein denote deviations from the exact value by +/−10%, preferably by +/−5% and/or deviations in the form of changes that are insignificant to the function.

Figure 15:
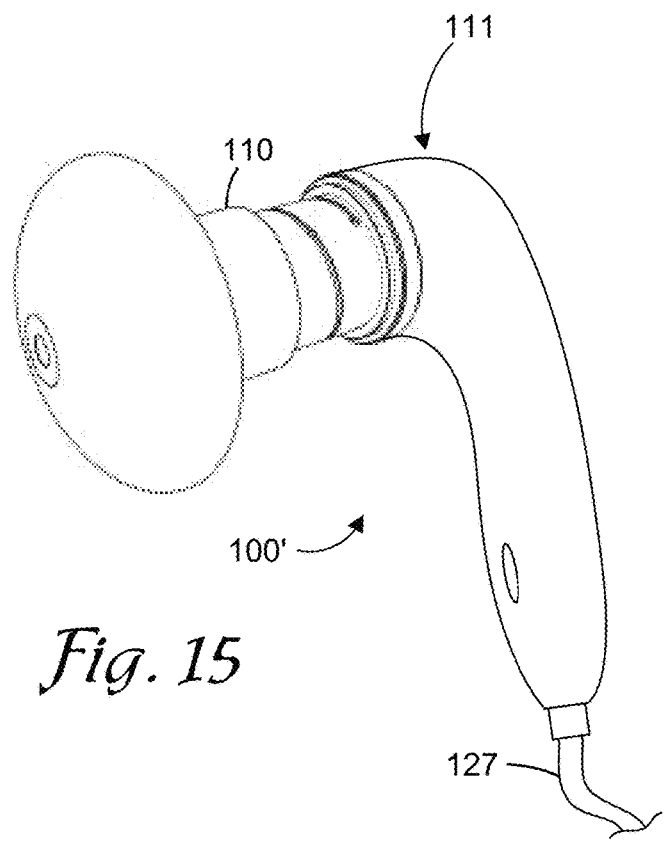
FIG. 15 is a perspective view of an exemplary wired earbud that includes an adjustable ear tip sleeve depicted in accordance with an exemplary embodiment.

With initial reference to FIGS. 2-5, an exemplary audio device or earbud 100 is described in accordance with an exemplary embodiment. The audio device 100 is interchangeably referred to herein as an earbud 100 for simplicity, but such is not intended to limit embodiments to any particular forms or functions that may be associated with the term "earbud." As depicted in FIGS. 2-5, the earbud 100 includes a body 110 configured in a bullet-shaped form but other forms can be employed. For example, the body 110 might be cylindrical, frustroconical, or spheroidal, among other forms or combinations thereof. The audio device 100 is configured for insertion or disposal in an external portion or pinna 10 of a human ear 12, or preferably at least partially into an ear canal 14 of the ear 12, so as to direct an audio output toward and/or into the ear canal 14 to be heard by a user. As depicted in FIG. 15, in some embodiments, the body 110 may form a portion of a larger audio device 100' such that the body 110 may be insertable into the ear canal 14 of a user while a remainder 111 of the device 100' remains exterior to the ear canal 14 and/or the ear 12 of the user.

Figure 2:
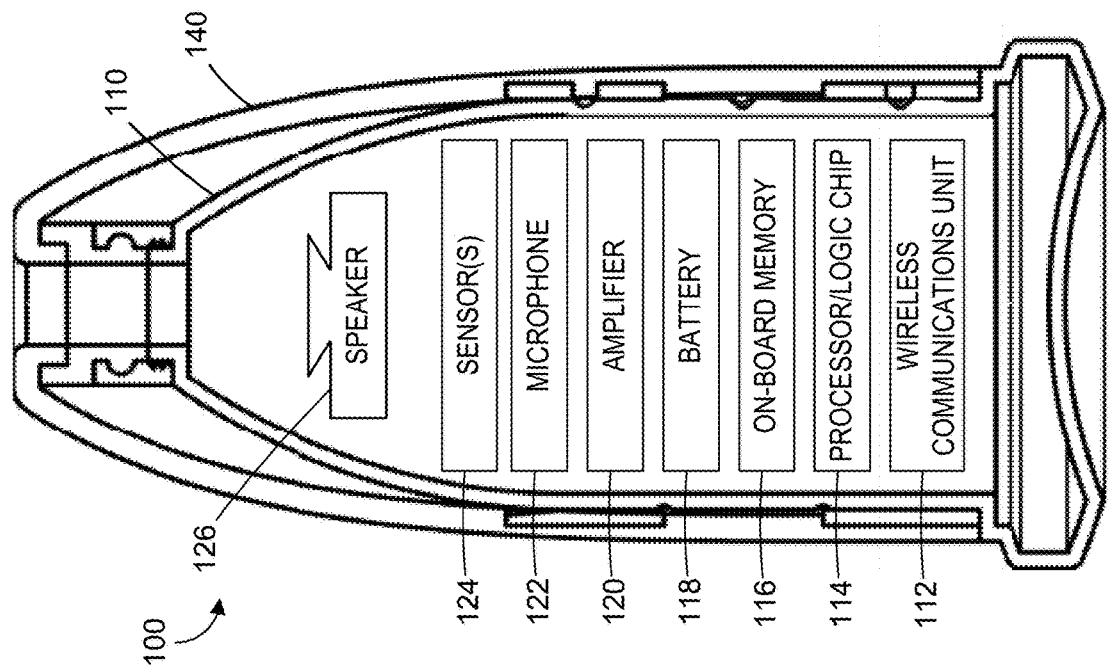
FIG. 2 is a cross-sectional, block diagrammatic, view of an earbud with an adjustable ear tip sleeve depicting components disposed therein in accordance with an exemplary embodiment.
Figure 1:
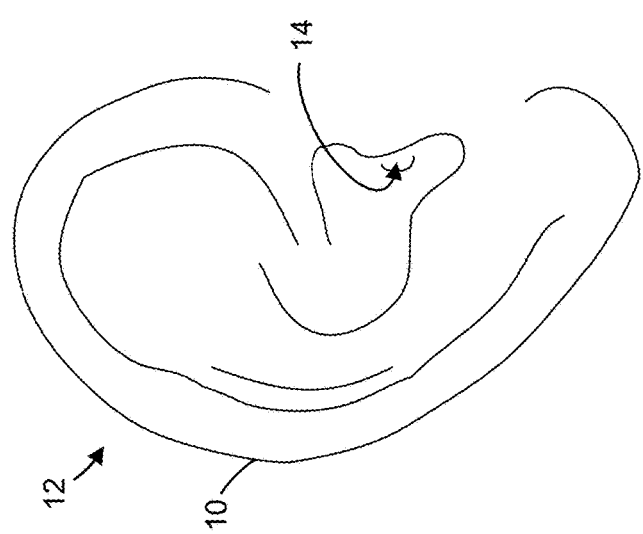
FIG. 1 is an illustrative view of a human ear.

As depicted in FIG. 2, variety of components may be disposed in the body 110 and configured for operation of the earbud 100 including a wireless communications unit 112, a processor or logic chip 114, an on-board memory 116, a battery 118, an amplifier 120, a microphone 122, and one or more of a variety of sensors 124, as well as an audio output device or speaker 126, among other components. The audio output device is referred to generally herein as a speaker however such is not intended to limit the audio device to any particular form of device suitable to produce an audible output. It is to be understood that one or more of these components can be combined or their functions performed by another component. For example, processors can include memory. Additionally, detail of the connections and communications between the components is not necessary for conveying an understanding of embodiments of the invention and is not described in detail herein.

Only one earbud 100 is shown and described herein however such is not intended to limit embodiments of the invention. The earbud 100 is typically employed in pairs with one earbud 100 being disposed in each ear of a user, but may be used alone in a monaural fashion or in groups greater than two for use by more than one user simultaneously. The earbud 100 is preferably configured as a wireless audio device, however embodiments such as the earbud 100' that employs a wire 127 as depicted in FIG. 15 are foreseen and are within the scope of this description.

The body 110 of the earbud 100 includes an output end 128 and a base 130 disposed at opposing longitudinal ends of the body 110. The output end 128 includes an opening through which sound produced by the speaker 126 is directed toward/into the ear canal 14 of the user. The base 130 may include a gripping feature useable by a user to grasp the earbud 100 for insertion and/or removal from the user's ear 12 or from a charging/storage device, such as an annular ridge 132 that extends radially outward from the body 110. In another embodiment, the gripping feature comprises a recessed channel provided instead of or in addition to the annular ridge 132 to aid grasping by a user, e.g. the channel may be engageable by a user's fingernail.

Figure 16:
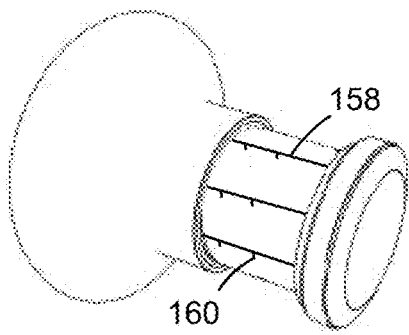
FIG. 16 is a perspective view of an earbud with adjustable ear tip sleeve configured with linear tracks for adjustment of the ear tip sleeve depicted in accordance with an exemplary embodiment.
Figure 17:
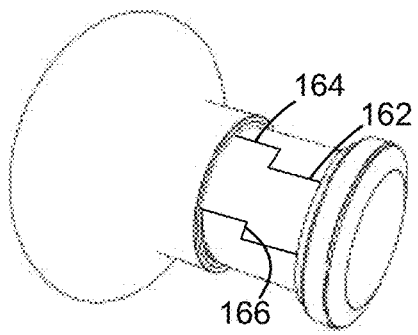
FIG. 17 is a perspective view of an earbud with adjustable ear tip sleeve configured with tracks for adjustment of the ear tip sleeve that follow a stepwise path depicted in accordance with an exemplary embodiment.

An exterior surface of the body 110 includes a tracked portion 134 extending along at least a portion of the longitudinal length of the body 110 between the output end 128 and the base 130. Tracks 136 or threads of the tracked portion 134 may follow a spiral or threaded pattern that encircles the body as it moves axially along the body. The tracks 136 may be raised or recessed into the surface of the body 110 and may include one or more stops 138 along the length thereof. The stops 138 may similarly be raised or recessed into the surface of the body 110. In another embodiment, the tracks 136 are replaced with axially extending grooves or ridges following one or more linear or non-linear paths. For example, FIG. 16 depicts an axially extending path 158 with a plurality of notches 160 that extend generally circumferentially and/or at an angle relative to the circumference. Or FIG. 17 depicts a step-wise path 162 that includes axially extending segments 164 separated by circumferentially extending segments 166. The notches 160 and the circumferentially extending segments 166 may operate as the stops 138 to resist axial movement along the respective path 158, 162 until an additional axial and/or rotational movement is provided.

Figure 3:
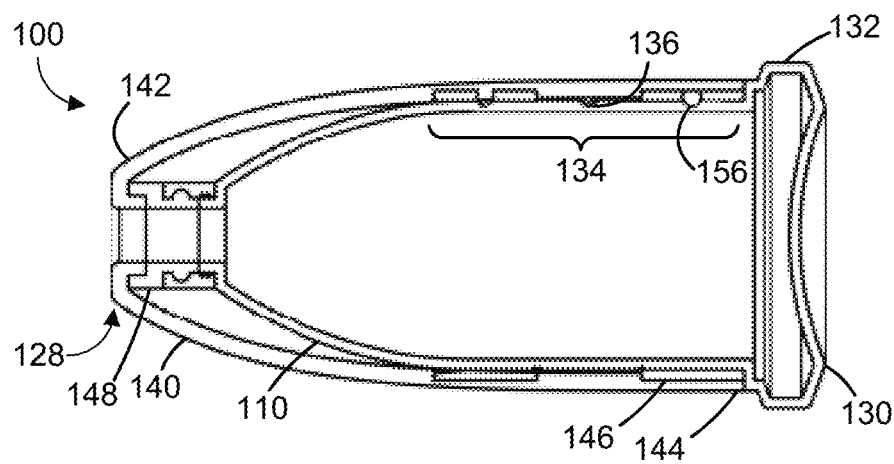
FIGS. 3-5 are cross-sectional views of an earbud with an adjustable ear tip sleeve depicted in retracted, intermediate, and fully expanded positions in accordance with an exemplary embodiment.
Figure 4:
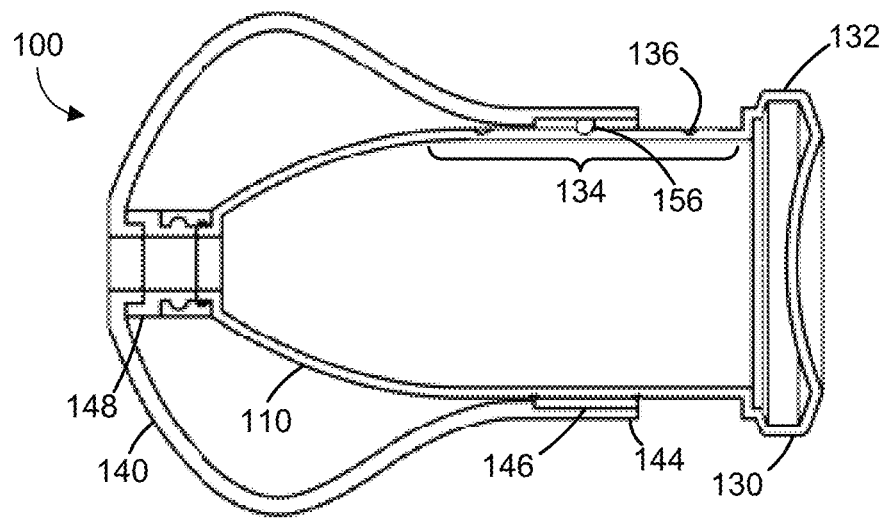
Figure 5:
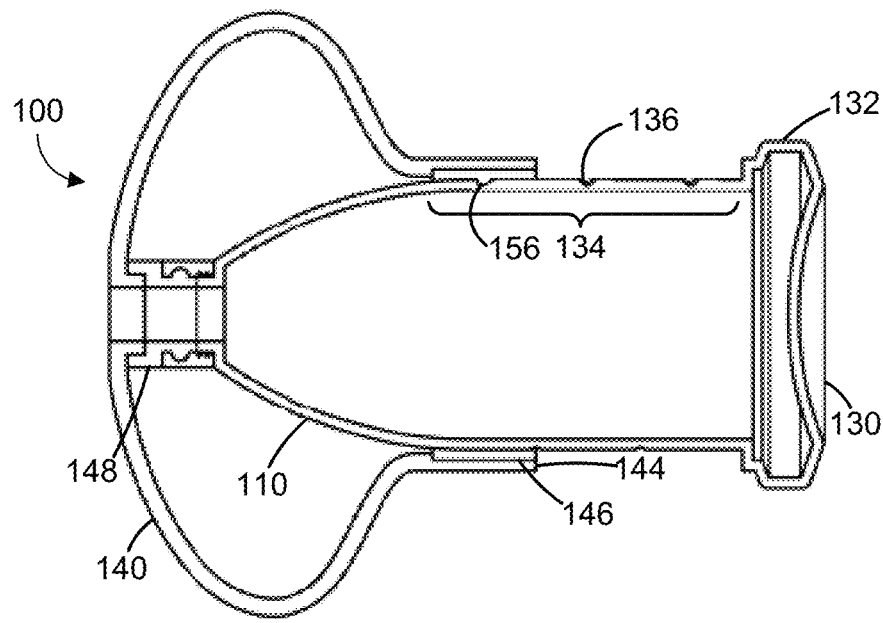

An ear tip sleeve 140 is disposed to overlap at least a portion of the exterior surface of the body 110. The sleeve 140 is formed from a thin layer of a pliable, resilient material such as a rubber, silicon, or similar material that is provided as a hollow form configured to receive at least a portion of the body 110 therein. As depicted in FIGS. 3-5, the layer of material forming the sleeve 140 has a generally constant thickness, but in some embodiments may include one or more sections having increased thicknesses which may aid to shape the sleeve 140 when flexed as described below as well as to aid durability of the sleeve 140 and the fit or frictional characteristics between the sleeve 140 and the ear 12 of the user.

In a retracted state (FIG. 3), the ear tip sleeve 140 provides a form that generally mimics that of the exterior surface of the body 110. A leading end 142 of the sleeve 140 is fixed against axial movement relative to the body 110 at or near the output end 128 and extends longitudinally to a trailing end 144 that is spaced apart from a terminal end of the base 130. In one embodiment, the trailing end 144 extends to the annular ridge 132 or to the terminal edge of the base 130.

An interior surface of the sleeve 140 near the trailing end 144 may include tracks, threads, or similar features configured to engage the tracks 136 on the exterior surface of the body 110 of the earbud 100. In one embodiment, the trailing end 144 of the sleeve 140 is coupled to a collar 146 that at least partially encircles the body 110 and includes track-engagement features 156, protuberances, threads, or other features configured to mate and/or engage with the tracks 136 of the body 110.

The leading end 142 of the sleeve 140 may be coupled to the body 110 at or near the opening of the output end 128. Alternatively, a mounting ring 148 may be rotatably coupled to the body 110 at or near the output end 128. The mounting ring 148 is rotatable relative to the body 110 about the longitudinal axis of the body 110 and is coupled or retained to the body 110 at or near the leading end 142 of the sleeve 140 to allow the sleeve 140 to rotate relative to the body 110. In another embodiment, the leading end 142 of the sleeve 140 may be maintained in a fixed axial position but enabled to rotate relative to the body 110. For example, the output end 128 of the body 110 may be provided with a wall, ridge, or similar abutment configured to resist axial movement of the leading end 142 of the sleeve 140 toward the output end 128, but also to allow sliding rotational movement of the sleeve 140 along the exterior surface of the body 110.

Figure 12:
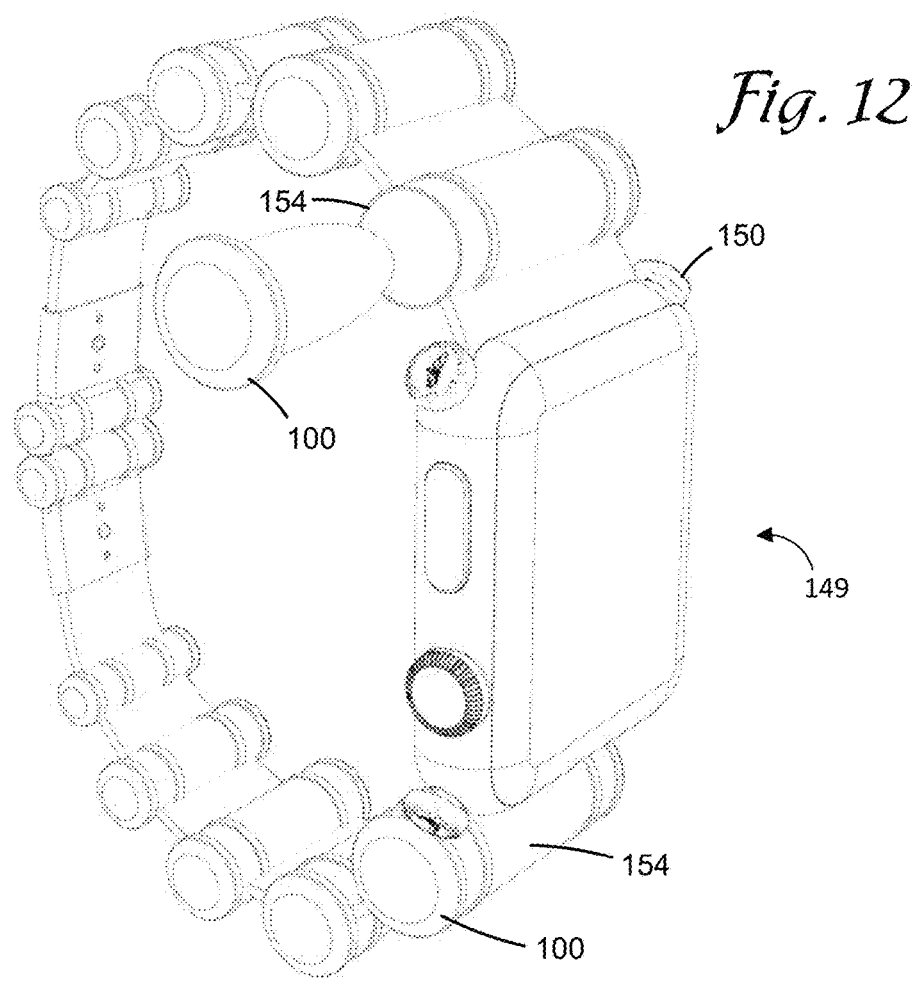
FIG. 12 is a perspective view of a watch configured as a charging device with receptacles for a pair of earbuds with adjustable ear tip sleeves depicted in accordance with an exemplary embodiment.
Figure 13:
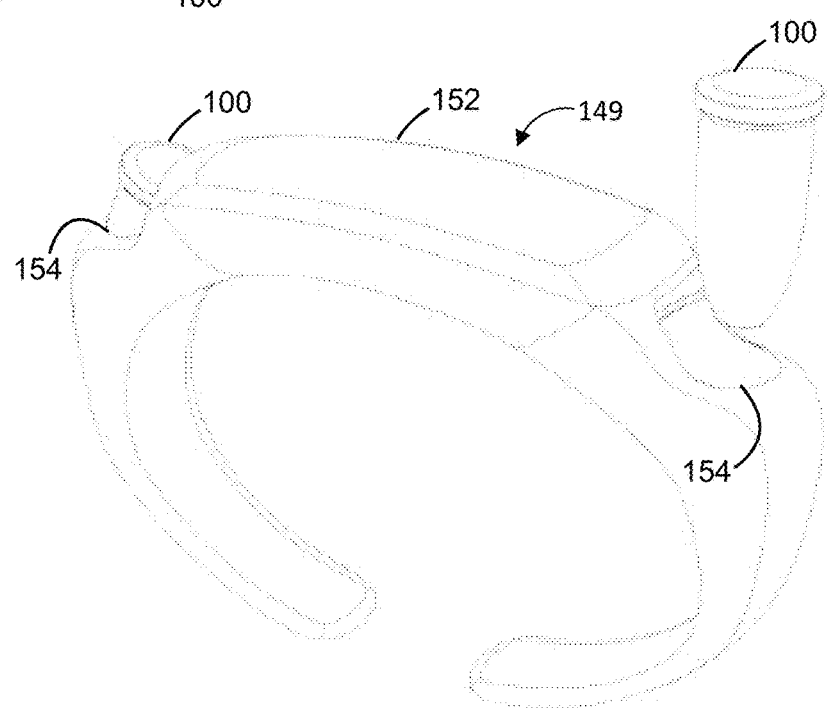
FIG. 13 is a perspective view of a fitness tracker bracelet configured as a charging device with receptacles for a pair of earbuds with adjustable ear tip sleeves depicted in accordance with an exemplary embodiment.

The earbud 100 may be provided with a charging device 149 that includes a built-in battery to supply power to the earbud 100 or that may be electrically coupled to an available electrical grid to obtain and supply power to the earbud 100. For example, as depicted in FIGS. 12-13, the charging device 149 may comprise a watch/watch band 150 or a fitness tracker bracelet 152. The charging device 149 may also be integrated into a variety of other wearable personal articles including, for example and not limitation, necklaces, eyeglass frames, augmented reality or virtual reality headsets, belt buckles, hats, earrings and jewelry, shirts, pants, handbags, backpacks, or the like. Non-wearable personal articles such as cases or satchels that are placed in a handbag, pocket, or hung from a lanyard can also comprise the charging device 149.

In some embodiments, wearable and non-wearable personal articles that do not include charging and/or data transfer capabilities may be provided for use as storage devices for the earbuds 100. Such storage devices may include similar structures to those described below for the charging device 149 to aid storage and securement of the earbuds 100.

The charging device 149 and the earbud 100 may include mating electrical contacts that enable electrical coupling therebetween for provision of power and/or data therebetween. Alternatively, the charging device 149 may employ inductive charging or other wireless means for providing power and/or data to the earbud 100. The charging device 149 includes one or more receptacles 154 in which the earbud 100 may be disposed for charging/data communication. The receptacles 154 may be configured as a blind bore in which the earbud 100 can be axially inserted, as depicted in the watch/watch band 150 and fitness tracker bracelet 152 depicted in FIGS. 12 and 13. The receptacle 154 may be dimensioned to receive the earbud 100 only when the ear tip sleeve 140 is in the retracted state which may minimize size requirements of the charging device 149. The receptacles 154 may take a variety of alternative configurations which may also require the sleeve 140 to be in the retracted state. In another embodiment, the sleeve 140 may be expanded within the receptacle 154 before or after insertion therein to aid retention of the earbud 100 within the receptacle 154.

With continued reference to FIGS. 3-11, operation of the earbud 100 is described in accordance with an exemplary embodiment. If installed in a charging device 149, the earbuds 100 are removed from the receptacles 154 therein. In one embodiment, the charging device 149 includes blind bore-styled receptacles 154 in which the earbuds 100 are installed output end 128 first. The user may grasp the annular ridge 132 of the base 130 by hand or using a fingernail to withdraw the earbud 100 from the receptacle 154. The annular ridge 132 may similarly be used during removal of the earbud 100 from the ear 12 of the user upon completion of use.

Figure 14:
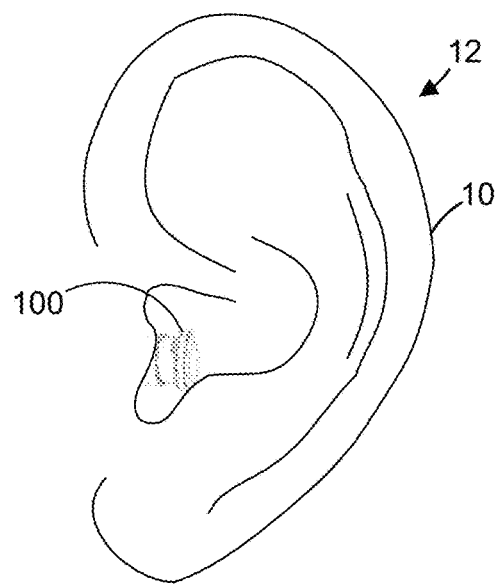
FIG. 14 is an illustrative view of an ear with an earbud with an adjustable ear tip sleeve disposed therein depicted in accordance with an exemplary embodiment.

The earbuds 100 may be inserted at least partially into respective ear canals 14 of the user, output end 128 first, as depicted in FIG. 14. Preferably, the base 130 remains outside of the ear canal 14 to enable grasping thereof for removal from the ear canal 14 when so desired. The earbud 100 and the ear tip sleeve 140 are dimensioned for use by users with a range of ear canal 14 sizes, i.e., interior diameter of the ear canal 14. The earbud 100 and ear tip sleeve 140, in the retracted state (depicted in FIGS. 3, 6, and 7) preferably provide an outer diameter or size that is smaller than or equal to an average minimum size of human ear canals 14. However, smaller or larger dimensions may be employed.

When properly adjusted or sized, the ear tip sleeve 140 may contact the interior surface of the ear canal 14 to provide a frictional resistance to removal of the earbud 100 from the ear canal 14 and to cushion the fit between the earbud 100 and the interior of the ear canal 14. Surface features and/or surface roughness may be provided on an exterior surface of the ear tip sleeve 140 to aid frictional engagement with the interior surface of the ear canal 14.

In user's having small ear canals 14, such a fit might be achieved with the ear tip sleeve 140 in the retracted state. If necessary, such as for users having ear canals with greater than the minimum average size/diameter, the user adjusts the overall diameter of the ear tip sleeve 140 to provide a desired fit with the user's respective ear canals 14. This may be accomplished prior to installation of the earbud 100 into the user's ear canal 14, after installation, or as a trial-and-error process whereby the user selects a sleeve dimension, tests the fit, and then repeats the process as needed.

Figure 8:
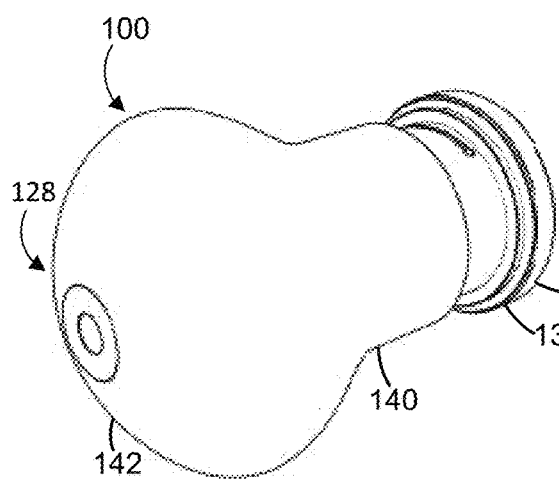
Figure 9:
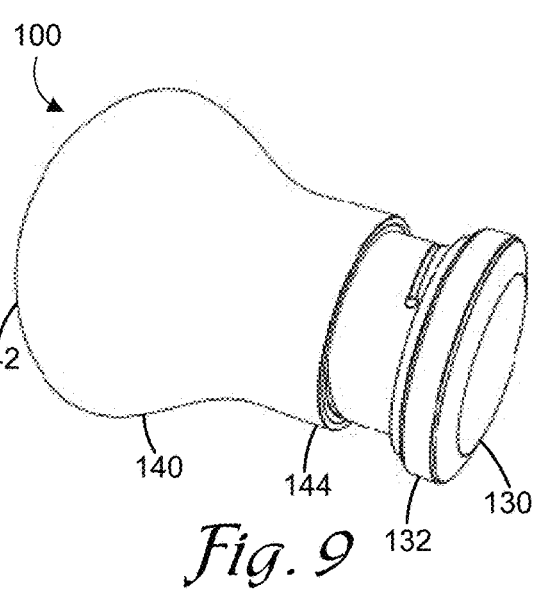
Figure 10:
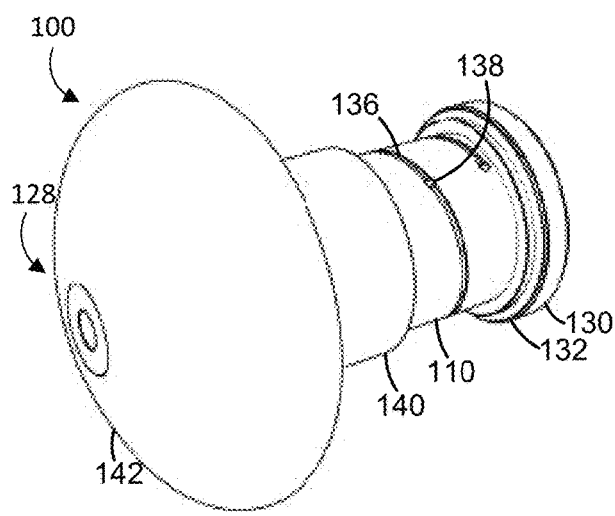
Figure 11:
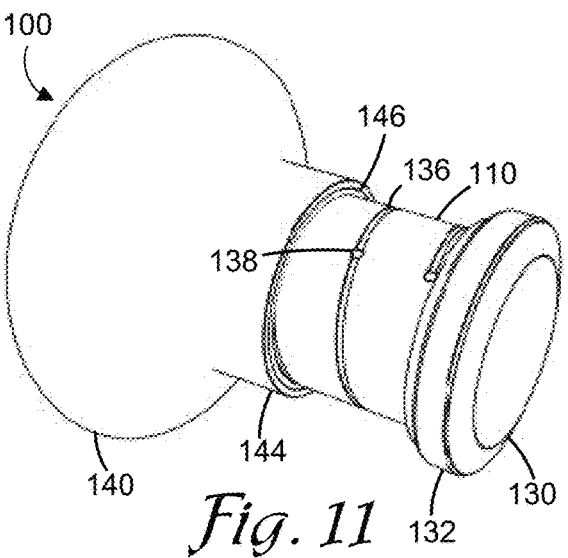

To adjust the ear tip size, the collar 146 of the ear tip sleeve 140 (or the trailing end 144 of the sleeve 140 when no collar 146 is provided) is rotated relative to the body 110. The tracked coupling between the collar 146 and the body 110 causes axial movement of the collar 146 toward the output end 128 of the body 110 as the collar 146 is rotated in a first direction. FIGS. 4, 8, and 9 depict axial movement of the collar 146 partially along the length of the body 110 to an intermediate position while FIGS. 5, 10, and 11 depict axial movement of the collar 146 to a full extent. The greater the extent of the movement of the collar 146 toward the output end 128 the greater the radial expansion of the sleeve 140 as described more fully below.

Interaction between the collar 146 and the stops 138 may provide a resistance to rotational movement of the collar 146 relative to the body 110 that operates to maintain the collar 146 in a particular position relative to the body 110 and thus maintains the ear tip sleeve 140 in an associated position. The interaction between the collar 146 and the stops 138 may provide a tactile indication to the user that the particular position has been reached. In another embodiment, a frictional engagement between the collar 146 and/or an interior surface of the ear tip sleeve 140 and the body 110 is sufficient to retain the position of the collar 146 relative to the body 110.

Resilience of the material from which the ear tip sleeve 140 is formed may be employed to maintain engagement of the collar 146 with the stops 138. For example, the ear tip sleeve 140 may be biased to return to the original, retracted state. Such bias in the sleeve 140 material may urge the collar 146 and/or any protuberance thereon into engagement with the stops 138. The bias may be in an axial direction and/or a rotational direction.

The interaction between the stops 138 and the collar 146 may be overcome by application of an additional rotational force to enable further rotation of the collar 146. As depicted in FIGS. 3-11, the stop 138 may comprise a detent or shallow depression and moving beyond the stop 138 may require a small additional rotational force to overcome engagement of a track-engagement feature 156 on the interior wall of the collar 146 with the detent 138 followed by further rotational movement along the tracks 136. In other embodiments, the stop 138 and the collar 146 may engage by a mechanical means which requires actuation of a lever or similar component to disengage the collar 146 from the stop 138, or the collar 146 may require an axial or other movement to disengage the stop 138, among other forms of engagement/disengagement between the stops 138 and the collar 146.

Axial movement of the collar 146 relative to the body 110 causes the portion of ear tip sleeve 140 between the leading end 142 and the trailing end 144 to flex radially outward away from the body 110 in a mushroom-like fashion and thus increases the overall diameter of the ear tip sleeve 140. Additional rotation and axial movement of the collar 146 toward the output end 128 further increases the diameter of the ear tip sleeve 140 up to a maximum diameter. The maximum diameter may correspond with or be slightly larger than an average maximum diameter of user's ear canals 14. For example, in the retracted position, the sleeve 140 may have a diametrical dimension of about 5 millimeters (mm) to about 9 mm or preferably about 6 mm; in the intermediate position the diametrical dimension may be about 7 mm to about 11 mm or preferably about 9 mm; and in the full extent the diametrical dimension may be about 10 mm to about 15 mm or preferably about 12 mm, however other dimensions may be employed without departing from the scope of embodiments described herein. Additional positions may also be provided between the retracted and full extent positions. The user may thus selectively adjust the rotation/axial movement of the collar 146 to achieve a diameter of the ear tip sleeve 140 that provides a desired fit with the user's ear canal 14.

The desired fit between the ear tip sleeve 140 and the user's ear canal 14 preferably fully seals the ear canal, e.g. no air gaps between the ear tip sleeve 140 and the interior wall of the ear canal 14 and provides sufficient frictional engagement to retain the earbud 100 in the ear canal 14 when the user is engaged in moderate activity. However, the user can adjust the ear tip sleeve 140 through rotational/axial movement of the collar 146 to provide a lighter fit or a tighter fit as desired. Typically a desired fit at least partially deforms the ear tip sleeve 140 at least partially from its expanded state to conform to the ear canal 14.

When use of the earbud 100 is no longer desired, the earbud 100 is removed from the user's ear canal 14. The ear tip sleeve 140 may be returned to the retracted position by rotation of the collar 146 in an opposite second direction to move the collar 146 toward the base 130. The earbud 100 may be replaced in the charging device 149 for charging.

The shape or form taken by the ear tip sleeve 140 when flexed outwardly may be contoured by adjusting the thickness profile of the ear tip sleeve 140 materials to stiffen or weaken portions thereof, among other methods. The ear tip sleeve 140 is configured to provide a symmetric circular form that may deform to conform to asymmetrically shaped ear canals 14 of users. In some embodiments, the ear tip sleeve 140 includes a non-circular and/or an asymmetric form when flexed radially outward.

In one embodiment, the ear tip sleeve 140 is coupled to the output end 128 of the body and thus also flexes or stretches circumferentially between the output end 128 and the collar 146 as the collar 146 is rotated. In another embodiment, the leading end 142 of the ear tip sleeve 140 is coupled to the mounting ring 148 which is rotatably coupled to the output end 128 of the body 110. As such, rotation of the collar 146 also acts to rotate the mounting ring 148 through the ear tip sleeve 140 which extends therebetween and relieves circumferential flexing or stretching of the ear tip sleeve 140.

Figure 6:
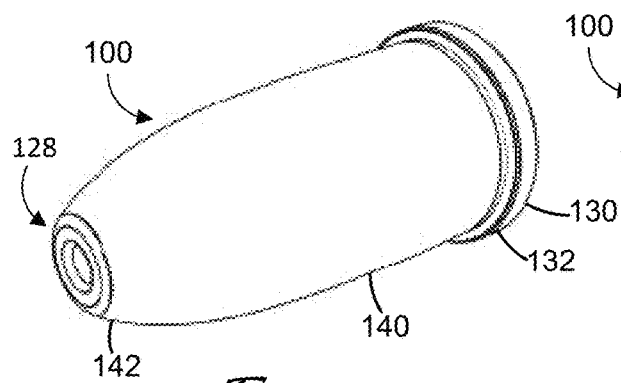
FIGS. 6-11 are perspective views of the earbud of FIGS. 3-5.
Figure 7:
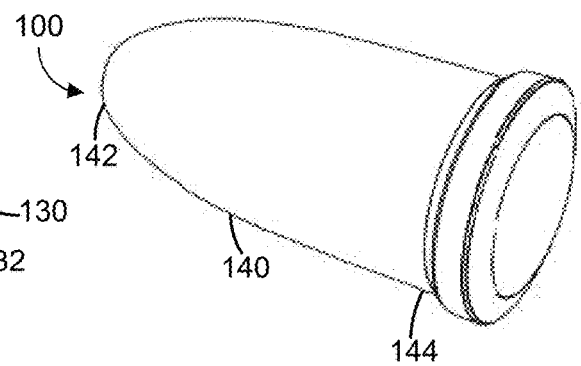

In another embodiment, the ear tip sleeve 140 is formed to provide a bias toward the expanded position (FIGS. 5, 10, and 11) instead of toward the retracted position (FIGS. 3, 6, and 7). In such an arrangement, the collar 146, stops 138, and tracks 136 or corresponding structures are configured oppositely to operate or counteract axial forces applied in the opposite axial direction. For example, the structures are configured to retain the ear tip sleeve 140 in the retracted position rather than to retain the ear tip sleeve 140 in the expanded position as described above. Additionally, in use once installed in the ear canal 14 of the user, the ear tip sleeve 140 may be released from the retracted position and allowed to move toward the expanded position. The ear tip sleeve 140 may thus expand to fill the space between the earbud 100 and the interior of the ear canal 14 and to apply a sufficient force on the ear canal wall to frictionally retain the earbud 100 within the ear canal 14. Such an arrangement would automatically adjust to the size of the user's ear canal 14.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Identification of structures as being configured to perform a particular function in this disclosure and in the claims below is intended to be inclusive of structures and arrangements or designs thereof that are within the scope of this disclosure and readily identifiable by one of skill in the art and that can perform the particular function in a similar way. Certain features and sub-combinations are of utility and may be employed without reference to other features and sub-combinations and are contemplated within the scope of the claims.

What is claimed is:

1. An audio device with an adjustable ear tip, the audio device comprising:
   a body having an at least partially cylindrical form with an output end through which an audible output produced by the audio device is directed;
   a sleeve that at least partially overlies an exterior surface of the body, the sleeve having a leading end and a trailing end, the leading end being retained against axial movement relative to the body, the trailing end being movable axially toward the leading end, movement of the trailing end toward the leading end expanding at least a portion of the sleeve radially outward from the body to form an ear tip;
   a track extending axially along the body; and
   a track-engagement feature disposed between the sleeve and the body and following the track as the track-engagement feature is moved along the body, the track-engagement feature following the track to move the trailing end of the sleeve toward the leading end when the trailing end is rotated about a longitudinal axis of the body.

2. The audio device of claim 1, wherein the sleeve includes a hollow, substantially cylindrical, interior form and extends along the exterior surface of the body from the output end toward an opposite end of the body, and wherein the sleeve is biased to lie alongside the body.

3. The audio device of claim 1, wherein the track follows a spiral pattern along the body.

4. The audio device of claim 1, wherein the track follows a linear path along the body.

5. The audio device of claim 1, wherein the track follows a stepwise path along the body.

6. The audio device of claim 1, wherein the track includes one or more stops that are engageable by the track-engagement feature to releasable retain the track-engagement feature, and wherein engagement of the track-engagement feature with one of the stops retains the sleeve in one of a plurality of radially expanded positions.

7. The audio device of claim 1, further comprising:
a collar coupled to the sleeve and including the track-engagement feature.

8. The audio device of claim 1, further comprising:
a mounting ring rotatably coupled to the output end of the body and fixedly coupled to the leading end of the sleeve, the mounting ring enabling rotation of the sleeve about a longitudinal axis of the body.

9. The audio device of claim 1, further comprising:
a ridge disposed on the body opposite the output end and extending at least partially circumferentially about the body, the ridge being graspable by a user.

10. The audio device of claim 1, further comprising:
a charging device that includes a receptacle configured to receive the body and the sleeve, the sleeve being in a retracted position in which the sleeve is not expanded radially outward from the body.

11. The audio device of claim 10, wherein the charging device is integrated in to a wearable personal article comprising one or more of a watch, a watch band, a fitness tracker, and a bracelet.

12. A method for adjusting a fit between an audio device and an ear canal, the method comprising:
providing an audio device having a body and a sleeve, the body having an at least partially cylindrical form with an output end through which an audio output produced by the audio device is directed and including a track that extends at least partially axially along the body, the sleeve having a leading end, a trailing end opposite the leading end, and a hollow interior form into which at least a portion of the body is disposed, the leading end of the sleeve being retained against axial movement relative to the body, and the sleeve including a track-engagement feature;
moving the track-engagement feature along the track to move the trailing end axially toward the leading end from a first axial position to a second axial position, the moving flexing at least a portion of the sleeve radially outward from the body to provide an ear tip with a first radial dimension; and
retaining the trailing end at the second axial position.

13. The method of claim 12, further comprising:
moving the trailing end axially toward the leading end from the second axial position to a third axial position, the moving flexing the portion of the sleeve radially outward from the body to provide the ear tip with a second radial dimension that is greater than the first radial dimension; and
retaining the trailing end of the sleeve at the third axial position.

14. The method of claim 12, wherein moving the trailing end axially toward the leading end further comprises:
rotating the trailing end about a longitudinal axis of the body.

15. An audio device with an adjustable ear tip, the audio device comprising:
a body having an at least partially cylindrical form with an output end through which an audible output produced by the audio device is directed, and a track formed in an exterior surface of the body and extending at least partially axially along the body;
a sleeve that at least partially overlies an exterior surface of the body, the sleeve having a leading end and a trailing end, the leading end being retained against axial movement relative to the body, the trailing end being movable axially toward the leading end, movement of the trailing end toward the leading end expanding at least a portion of the sleeve radially outward from the body to provide an ear tip with a first radial dimension; and
a collar disposed at least partially between the trailing end of the sleeve and the body and including a track-engagement feature configured to engage and follow the track as the trailing end of the sleeve is moved toward the leading end.

16. The audio device of claim 15, wherein the trailing end of the sleeve is biased to move away from the leading end.

17. The audio device of claim 15, wherein the trailing end of the sleeve is biased to move toward the leading end.

* * * * *